Figure 2:
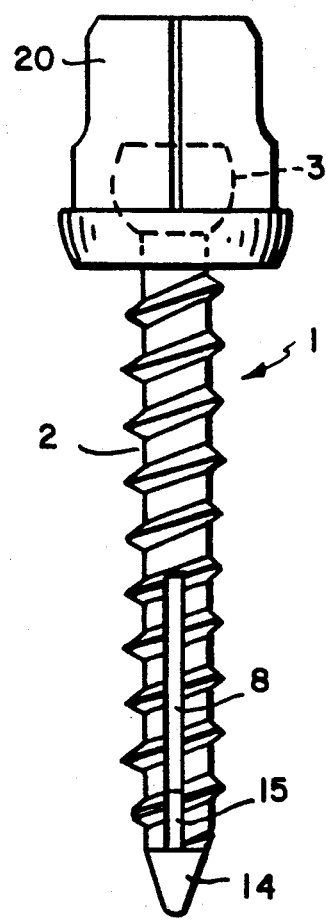

United States Patent [19]

Biedermann et al.

[11] Patent Number: 5,209,753
[45] Date of Patent: May 11, 1993

[54] BONE SCREW

[76] Inventors: Lutz Biedermann, Berta-Suttner-Str.23, D-7730 VS-Schwenningen; Jürgen Harms, Belchenweg 9, D-7517 Waldbronn-Reichenbach, both of Fed. Rep. of Germany

[21] Appl. No.: 679,085
[22] PCT Filed: Nov. 2, 1990
[86] PCT No.: PCT/EP90/01835
§ 371 Date: Jun. 28, 1991
§ 102(e) Date: Jun. 28, 1991
[87] PCT Pub. No.: WO91/06252
PCT Pub. Date: May 16, 1991

[30] Foreign Application Priority Data

Nov. 3, 1989 [DE] Fed. Rep. of Germany ....... 3936703

[51] Int. Cl.$^5$ ............................................. A61B 17/56
[52] U.S. Cl. ......................................... 606/72; 606/73
[58] Field of Search ...................... 606/61, 62, 63, 65, 606/66, 67, 68, 72, 73, 60; 411/44, 55, 58, 59, 60, 57, 71, 72, 128, 395

[56] References Cited

U.S. PATENT DOCUMENTS

| | | | |
|---|---|---|---|
| 2,381,050 | 8/1945 | Harding | 606/65 |
| 3,759,257 | 9/1973 | Fischer | 606/63 |
| 3,760,802 | 9/1973 | Fischer | 606/63 |
| 3,779,239 | 12/1973 | Fischer | 606/63 |
| 4,013,071 | 3/1977 | Rosenberg | 606/73 |
| 4,091,806 | 5/1978 | Aginsky | 606/63 |
| 4,204,531 | 5/1980 | Aginsky | 606/63 |
| 4,590,930 | 5/1986 | Kurth | 606/63 |
| 4,723,541 | 2/1988 | Reese | 606/73 |
| 4,760,843 | 8/1988 | Fischer | 606/82 |
| 4,858,602 | 8/1989 | Seidel | 606/60 |
| 4,940,467 | 7/1990 | Tronzo | 606/73 |
| 4,946,458 | 8/1990 | Harms | 606/61 |

FOREIGN PATENT DOCUMENTS

| | | |
|---|---|---|
| 0266701A1 | 7/1987 | European Pat. Off. . |
| 2063650 | 6/1972 | Fed. Rep. of Germany . |
| 603143 | 8/1978 | Fed. Rep. of Germany . |
| 3601865A1 | 1/1987 | Fed. Rep. of Germany . |
| 3614101C1 | 10/1987 | Fed. Rep. of Germany . |

Primary Examiner—Robert A. Hafer
Assistant Examiner—Michael Brown
Attorney, Agent, or Firm—Donald Brown; George W. Neuner

[57] ABSTRACT

A bone screw (1) has a threaded portion (2) and a head (3). Such screws are used in particular as pedicle screws. In order that the bone screw can be anchored securely also in soft bone tissue, the screw is provided with a longitudinal bore (5) extending along the longitudinal axis of the threaded portion (2), the longitudinal bore (5) being provided with a tapered portion (7) opposite to the head (3). In this region of the screw, slits are extending parallel to the threaded portion and an interior thread is provided. An expander part (12) having a tip (14) forming the point of the screw and a shaft (16) having a threaded portion (17) cooperating with said interior thread are provided.

6 Claims, 1 Drawing Sheet

U.S. Patent      May 11, 1993      5,209,753

BONE SCREW

The invention relates to a bone screw comprising a threaded portion and a head, such screws being used particularly as pedicel screws.

A screw of this type is known e.g. from DE-36 14 101 C.

In some cases the bone tissue in which the screw is to be anchored is so soft that sufficiently fixing the screw is difficult.

It is an object of the invention to provide a bone screw having a threaded portion and a head which improves the anchoring in bones as compared to conventional screws. The anchoring should be precisely adjustable.

This object is attained by the bone screw as outlined in claim 1.

Additional features are indicated in the subclaims.

Figure 1:
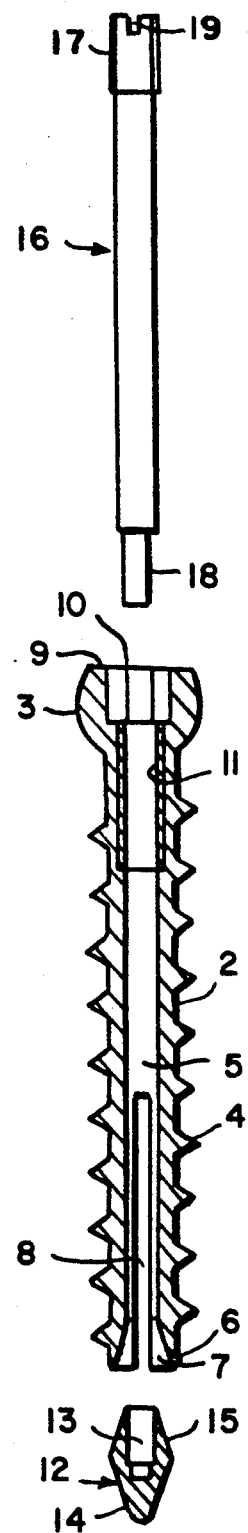

Further features and advantages of the invention will be apparent from the description of the figures which show:

FIG. 1 an exploded view of the bone screw, partially as sectional view, and

FIG. 2 the assembled screw together with a connecting part.

The bone screw 1 comprises a threaded portion 2 formed unitary with a head 3. The threaded portion is provided with an external thread 4 as commonly used with bone screws. As can be seen from FIG. 1, a coaxially aligned longitudinal bore extends through the interior of said screw. At the free end 6 opposite to the head a tapered conical portion 7 is provided. Slits 8 extend parallel to the longitudinal direction of said threaded portion. The axial length of said slits is at least equal to twice the length of said conical portion. Preferably, one pair of slits is provided, the slits being displaced by 180 degrees with respect to each other.

Opposite to the free end the head 3 is provided with a plane face arranged perpendicular with respect to the axis of symmetry. A recess 10 extends in axial direction which is formed to allow the screw to be screwed into a bone by a screw driver. The diameter of said recess is larger than the diameter of said longitudinal bore. Adjacent to the recess 10 a threaded portion 11 is arranged. Preferably, the length of this portion is at least twice the length of the tapered portion 7.

As can be seen from FIG. 1, the point of the bone screw is formed as a separate tip 12. A coaxially aligned bore 13 is provided at the end pointing towards the head. The opposite end has a point 14 corresponding to the tip of the bone screw. Opposite said point the exterior of said tip has a conical portion 15 tapering towards the conical portion 7 and formed to fit into said portion 7.

A shaft 16 is provided having a first threaded portion 17. The diameter and the pitch of this thread correspond to the interior thread of the portion 11 so that both threads may be joined. The diameter of the rest of the shaft 16 is dimensioned so it may be inserted into the longitudinal bore. Opposite to the first threaded portion 17 a second threaded portion 18 is provided which cooperates with an interior portion 18 and the pitch of the thread in the bore 13 are opposite to the pitch of the first threaded portion 17 and to the pitch of the corresponding interior thread in portion 11.

The length of the shaft 16 is selected such that the second threaded portion 18 extends into the tapered portion 7 and the tip 12 can be screwed onto this portion. Consequently, as shown in FIG. 2, the point 12 forms the normal point of the bone screw when the first threaded portion 17 is screwed to the end or at least close to the end of the threaded portion 11. A slit 19 is provided at the end of said threaded portion into which a screw driver may be inserted.

In operation, first the shaft 16 is screwed into the longitudinal bore 5 to the end of the threaded portion 11. Next, the tip 12 is screwed onto the second threaded portion 18 projecting into the tapered portion 7, thus forming the normal point of the screw, as shown in FIG. 2. If required, the head of the bone screw may be provided with a connecting part 20 which is movable with respect to said screw head, as described in DE 37 11 013 C. The connecting part serves to connect the screw with rods for the fixation of bone fragments, in particular spinal elements.

When the bone screw has been screwed into a bone, the shaft 16 can be unscrewed into the direction of the head 3 by inserting a screw driver into slit 19. Due to the opposite pitch of the threaded portions 17 and 18 the connection between the second threaded portion 18 and the expander part is maintained, the expander part being pulled into the portion provided with slits, thus effecting an expansion of the threaded portion 2. Since the region in which force is transferred from the expander part to the threaded shaft is not deformed, a very precise adjustment is possible.

In a further embodiment portion 11 may be provided with a greater diameter as compared to the diameter of the longitudinal bore 5, the diameter of the first threaded portion 17 having corresponding size.

According to a further example, the portion 11 has a smaller diameter than the adjacent portion of the longitudinal bore 5. The diameter of the first threaded portion corresponds to the interior thread of the portion 11. Shaft 16 and expander part 12 are formed unitary, the shaft 16 and the expander part being inserted from the free end 6 into the threaded portion 2. In this case, the first threaded portion 17 has a length such that the shaft may be moved—from a position in which the point 14 is positioned as shown in FIG. 2—toward the head, the expansion being effected by pulling the expander part into the slit portion.

We claim:

1. A bone screw comprising: an elongated shaft having an external thread for engaging bone material with a head on one end and a point with its apex facing the opposite end, a longitudinal bore extending along the longitudinal axis of said screw, one end of said bore opposite said head being provided with a tapered portion, and said screw also having slits extending parallel to the longitudinal direction of said screw, an internal thread being provided in said longitudinal bore, a second shaft insertable into said longitudinal bore and having a threaded portion cooperating with said internal thread in said bore, an expander part forming the point of said bone screw, said expander part and said shaft being connected by thread means, said expander part axially movable within said longitudinal bore as said second shaft is rotated.

2. A bone screw according to claim 1, wherein said tapered portion has a conical shape and said expander part has a correspondingly shaped head having a conical shape tapering in the direction of said head.

3. The bone screw according to claim 2, wherein said expander part is provided with a coaxial bore at its end pointing to the second shaft, and the end of said second shaft to be connected to the expander part is provided with a second threaded portion, the pitch of said first and said second threaded portions having opposite directions.

4. The bone screw according to claim 2, wherein the diameter of the internally threaded portion in said longitudinal bore is greater than the diameter of the adjacent portion of said longitudinal bore.

5. The bone screw according to claim 2, characterized in that said head is provided with a connecting part which is movable with respect to said screw.

6. A bone screw comprising: an elongated shaft having an external thread and a head, a longitudinal bore extending along the longitudinal axis of said screw, one end of said bore opposite said head being provided with a tapered portion, and said screw also having slits extending parallel to the longitudinal direction of said screw, an internal thread being provided in said longitudinal bore, a second shaft insertable into said longitudinal bore and having a threaded portion cooperating with said internal thread in said bore, an expander part forming the point of said bone screw and being larger in size than the longitudinal bore, said, said expander part and said shaft being inserted into said longitudinal bore as a unit.

* * * * *